(12) United States Patent
Rohan (10) Patent No.: US 12,178,460 B2
(45) Date of Patent: Dec. 31, 2024

(54) RETRIEVAL DEVICES AND RELATED METHODS OF USE (71) Applicant: Boston Scientific Scimed, Inc., Maple Grove, MN (US)

(72) Inventor: Prasopporn K. Rohan, Belmont, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 77 days.

(21) Appl. No.: 18/300,042

(22) Filed: Apr. 13, 2023

(65) Prior Publication Data
US 2023/0248381 A1 Aug. 10, 2023

Related U.S. Application Data (63) Continuation of application No. 15/069,583, filed on Mar. 14, 2016, now Pat. No. 11,653,942.

(60) Provisional application No. 62/137,556, filed on Mar. 24, 2015.

(51) Int. Cl.
A61B 17/221 (2006.01)

(52) U.S. Cl.
CPC .... *A61B 17/221* (2013.01); *A61B 2017/2212* (2013.01); *A61B 2017/2215* (2013.01)

(58) Field of Classification Search
CPC ............ A61B 17/221; A61B 17/32056; A61B 2017/2212; A61B 2017/2215; A61B 2017/2217; A61B 2017/00358
See application file for complete search history.

(56) References Cited

U.S. PATENT DOCUMENTS

| 5,098,440 A | 3/1992 | Hillstead |
| 5,499,981 A | 3/1996 | Kordis |
| 5,906,622 A | 5/1999 | Lippitt et al. |
| 5,924,175 A | 7/1999 | Lippitt et al. |
| 5,989,266 A | 11/1999 | Foster |

(Continued)

FOREIGN PATENT DOCUMENTS

| CN | 1317949 A | 10/2001 |
| JP | 2000083964 A | 3/2000 |

(Continued)

OTHER PUBLICATIONS

International Search Report and Written Opinion for International Application No. PCT/US2016/022463, dated May 27, 2016 (14 pages).

(Continued)

*Primary Examiner* — Majid Jamialahmadi
(74) *Attorney, Agent, or Firm* — Bookoff McAndrews PLLC (57) ABSTRACT According to one aspect, a retrieval device may include a sheath having a distal end. The retrieval device may also include an end effector movable relative to the distal end of the sheath. The end effector may include first and second arms. The first arm may include a first opening at a distal portion of the first arm. The second arm may include a second opening at a distal portion of the second arm. The end effector may also include a third arm. The third arm may be slidably received in the first and second openings. A distal portion of the third arm may form at least part of a loop. The loop may extend through the first and second openings.

18 Claims, 3 Drawing Sheets

(56) References Cited

U.S. PATENT DOCUMENTS

| | | | |
|---|---|---|---|
| 6,159,220 A * | 12/2000 | Gobron | A61B 17/221 606/127 |
| 6,224,612 B1 | 5/2001 | Bates et al. | |
| 6,302,895 B1 | 10/2001 | Gobron et al. | |
| 6,348,056 B1 | 2/2002 | Bates et al. | |
| 6,626,903 B2 | 9/2003 | McGuckin, Jr. et al. | |
| 6,652,537 B2 | 11/2003 | Mercereau et al. | |
| 6,676,668 B2 | 1/2004 | Mercereau et al. | |
| 7,041,108 B2 | 5/2006 | Lippitt et al. | |
| 7,210,210 B2 | 5/2007 | Lippitt et al. | |
| 7,322,989 B2 | 1/2008 | Teague et al. | |
| 7,491,211 B2 | 2/2009 | Ziegler | |
| 7,559,934 B2 | 7/2009 | Teague et al. | |
| 8,043,303 B2 | 10/2011 | Razvi et al. | |
| 8,597,303 B2 | 12/2013 | Hammack et al. | |
| 10,092,307 B2 | 10/2018 | Yokota | |
| 10,335,185 B2 | 7/2019 | Uihlein | |
| 2001/0001315 A1 | 5/2001 | Bates et al. | |
| 2003/0009176 A1 | 1/2003 | Bilitz | |
| 2003/0225419 A1 | 12/2003 | Lippitt et al. | |
| 2004/0199200 A1 | 10/2004 | Teague et al. | |
| 2007/0027456 A1 | 2/2007 | Gartner et al. | |
| 2007/0239141 A1 | 10/2007 | Hartley et al. | |
| 2009/0222035 A1 | 9/2009 | Schneiderman | |
| 2010/0042107 A1 | 2/2010 | Merrifield | |
| 2012/0239081 A1 | 9/2012 | Gartner et al. | |
| 2013/0317515 A1 | 11/2013 | Kuroda et al. | |
| 2014/0276913 A1 | 9/2014 | Tah et al. | |
| 2014/0350593 A1 | 11/2014 | Laroya et al. | |
| 2015/0066047 A1 | 3/2015 | Chu et al. | |
| 2015/0066049 A1 | 3/2015 | Chu | |
| 2015/0148814 A1 | 5/2015 | Chu | |
| 2015/0164522 A1 | 6/2015 | Budiman et al. | |
| 2015/0173783 A1 | 6/2015 | Tah et al. | |
| 2015/0190157 A1 | 7/2015 | Chu | |
| 2015/0190190 A1 | 7/2015 | Chu | |
| 2015/0196311 A1 | 7/2015 | Chu | |
| 2015/0327878 A1 | 11/2015 | Chu et al. | |
| 2016/0317165 A1 | 11/2016 | Yokota | |
| 2017/0049472 A1 | 2/2017 | Uihlein | |

FOREIGN PATENT DOCUMENTS

| | | |
|---|---|---|
| JP | 2015506236 A | 3/2015 |
| JP | 2017500156 A | 1/2017 |
| WO | 0119260 A1 | 3/2001 |
| WO | 2004032769 A1 | 4/2004 |
| WO | 2007110864 A2 | 10/2007 |
| WO | 2010019776 A2 | 2/2010 |
| WO | 2013018445 A1 | 2/2013 |
| WO | 2013106713 A1 | 7/2013 |
| WO | 2015034832 A1 | 3/2015 |
| WO | 2015100045 A1 | 7/2015 |

OTHER PUBLICATIONS

Supplemental Search issued in CN201680017808.8 on Jul. 9, 2020 (1 page).

* cited by examiner

RETRIEVAL DEVICES AND RELATED METHODS OF USE

CROSS-REFERENCE TO RELATED APPLICATIONS

This application is a continuation of U.S. application Ser. No. 15/069,583, filed on Mar. 14, 2016, which claims the benefit of priority of U.S. Provisional Application No. 62/137,556, filed on Mar. 24, 2015, the disclosure of each of which is herein incorporated by reference in its entirety.

TECHNICAL FIELD

Various aspects of the present disclosure relate generally to retrieval devices and related methods. More specifically, the present disclosure relates to devices and methods for retrieving objects within a patient.

BACKGROUND

Retrieval devices are often used to remove organic material (e.g., blood clots, tissue, and biological concretions such as urinary, biliary, and pancreatic stones) and inorganic material (e.g., components of a medical device or other foreign matter), which may obstruct or otherwise be present within a patient's body cavities or passages. For example, concretions can develop in certain parts of the body, such as in the kidneys, pancreas, ureter, and gallbladder. Minimally invasive medical procedures may be used to remove these concretions through natural orifices, or through an incision, such as during a percutaneous nephrolithotomy ("PNCL") procedure. Further, lithotripsy and ureteroscopy, for example, may be used to treat urinary calculi (e.g., kidney stones) in the ureter of a patient.

Retrieval devices may include end effectors for manipulating objects. Exemplary end effectors may have an open-end design or a closed-end design. For example, an end effector of the open-end design may have a plurality of arms that support a front loop through which an object may enter the end effector. After the end effector is closed around the object, the object may escape through the front loop under certain conditions. An exemplary end effector of the closed-end design may have difficulty capturing objects that are not positioned on a side of the end effector. Thus, there remains a need for retrieval devices with improved capabilities.

SUMMARY

Aspects of the present disclosure relate to, among other things, retrieval devices and related methods. Each of the aspects disclosed herein may include one or more of the features described in connection with any of the other disclosed aspects.

In one aspect of the present disclosure, a retrieval device may include a sheath having a distal end. The retrieval device may also include an end effector movable relative to the distal end of the sheath. The end effector may include first and second arms. The first arm may include a first opening at a distal portion of the first arm. The second arm may include a second opening at a distal portion of the second arm. The end effector may also include a third arm. The third arm may be slidably received in the first and second openings. A distal portion of the third arm may form at least part of a loop. The loop may extend through the first and second openings.

Aspects of the retrieval device may include one or more of the features below. The end effector may include a fourth arm slidably received in the first and second openings. Distal portions of the third and fourth arms may form the loop. The loop may be selectively expandable and contractible by sliding the third and fourth arms through the first and second openings. The third arm may be configured to slide through the first and second openings in one direction, and the fourth arm may be configured to slide through the first and second openings in an opposite direction, to selectively expand and contract the loop. The third arm may include a pair of proximal portions connected by a curved distal portion. The fourth arm may include a pair of proximal portions connected by a curved distal portion. The curved distal portion of the third arm may form one side of the loop, and the curved distal portion of the fourth arm may form an opposite side of the loop. The retrieval device may include a handle assembly configured to move the end effector relative to the distal end of the sheath. The end effector may be coupled to the handle assembly by a drive member. A first portion of the drive member may be formed by one of proximal portions of the first and second arms and a cable, a second portion of the drive member may be formed by a proximal portion of the third arm, and one of the first and second portions of the drive member may be movable relative to the other of the first and second portions of the drive member.

In another aspect of the present disclosure, a retrieval device may include a sheath having a distal end. The retrieval device may also include an end effector movable relative to the distal end of the sheath. The end effector may include a distal end. The end effector may also include an open end configuration, wherein first and second openings on first and second arms of the end effector receive a third arm of the end effector, and a distal portion of the third arm defines a central opening at the distal end of the end effector. The end effector may also include a closed end configuration, wherein a size of the central opening is reduced by the third arm drawing the first and second arms together at the distal end of the end effector.

Aspects of the retrieval device may include one or more of the features below. In the closed end configuration, distal ends of the first and second arms may be adjacent one another. In the closed end configuration, distal ends of the first and second arms may contact each other. The end effector may include a fourth arm. The first and second openings on the first and second arms of the end effector may receive the fourth arm of the end effector. A distal portion of the fourth arm may define at least part of central opening at the distal end of the end effector. In the open end configuration, curved ends of the third and fourth arms may define opposite sides of the central opening. Distal portions of the third and fourth arms may overlap at the distal end of the end effector. The end effector may be movable between an expanded state and a contracted state. The end effector may have the open end configuration in the expanded state and the closed end configuration in the contracted state. Distal tips of the first, second, third, and fourth arms may interlock with each other in the closed end configuration.

In another aspect of the present disclosure, a method of retrieving an object with a retrieval device may include maneuvering a distal end of a sheath of the retrieval device to a target area containing the object. The method may also include extending an end effector distally out of the distal end of the sheath. The method may also include expanding the end effector. The method may also include passing at least a portion of the object through an opening on the end effector. The opening may include a loop formed at least in part by distal portions of first and second arms of the end effector and a distal portion of a third arms of the end effector. The third arm may be received in first and second openings in the first and second arms. Alternatively, the opening may include a gap formed between the first and second arms, the first and third arms, and the second and third arms. The method may also include contracting the end effector around the object to exert a holding force on the object. Contracting the end effector may include reducing a size of the opening on the end effector.

Aspects of the retrieval device may include one or more of the features below. The end effector may be inherently biased to expand when extended distally out of the distal end of the sheath. Contracting the end effector may include retracting at least a portion of the end effector into the distal end of the sheath. Contracting the end effector may include retracting at least a portion of the third arm into the distal end of the sheath. Contracting the end effector may include bringing the distal portions of the first and second arms toward a central longitudinal axis of the end effector. Contracting the end effector may include bringing the distal portions of the first and second arms into contact by pulling at least a portion of the third arms in a proximal direction.

In another aspect of the present disclosure, a retrieval device may include a sheath having a distal end. The retrieval device may also include an end effector movable relative to the distal end of the sheath. The end effector may include a first arm, the first arm including a first opening at a distal portion of the first arm. The end effector may also include a second arm slidably received in the first opening, wherein a distal portion of the second arm forms at least part of a loop, and wherein the loop extends through the first opening.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

Overview

The present disclosure is drawn to retrieval devices and related and methods. Reference will now be made in detail to aspects of the present disclosure, examples of which are illustrated in the accompanying drawings. Wherever possible, the same reference numbers will be used throughout the drawings to refer to the same or like parts. The term "distal" refers to a portion farthest away from a user when introducing a device into a patient. By contrast, the term "proximal" refers to a portion closest to the user when placing the device into the patient.

Exemplary Aspects

FIGS. 1-7 show aspects of a retrieval device 10, with FIGS. 4-7 showing the retrieval device 10 retrieving an object 12. The retrieval device 10 may include an end effector assembly. According to one aspect, the end effector assembly may include an end effector 16 configured to engage the object 12. The end effector assembly may also include a drive member 18 configured to move the end effector 16. The end effector 16 may be selectively extended from and retracted into a distal portion of an outer sheath 42 by the drive member 18 for capturing and or releasing objects.

The end effector 16 may include arms 20, 24, 26, and 28. Arm 20 may include struts 21 and 22 that may be linked by a curved distal portion or end 32. According to one aspect, the arm 20 may be composed of a single continuous member. Alternatively, the arm 20 may be composed of two or more wire segments joined together to form the curved end 32. The single continuous member may include, for example, a wire having a U, teardrop, or petal shape. A gap between the struts 21 and 22 may decrease as the struts 21 and 22 extend proximally away from the curved end 32. The wire may be made of a shape-memory material such that the wire may return to its original shape and/or maintain the gap in the absence of a deforming force. For example, the wire may be made of Nitinol. Additionally or alternatively, the wire may be treated to possess an internal bias causing the arm 20 to move radially outwardly away from a longitudinal axis of the end effector 16 in the absence of a constraining force. Alternatively, the wire may be formed of any suitable material including, but not limited to, metals, polymers, or a combination of materials.

The arm 28 may be similar to the arm 20, and may include struts 29 and 30 that may be linked by a curved distal portion or end 34. According to one aspect, the arms 20 and 28 may have the same material, dimensional, and/or shape characteristics. The arms 20 and 28 may form opposing sides of the end effector 16.

The arms 24 and 26 may form other opposing sides of the end effector 16. The arm 24 may include an opening, loop, or eyelet 36 at its distal end. The arm 26 may also include an opening, loop, or eyelet 38 at its distal end. The arms 24 and 26 may be made of wires. For example, at least one of the arms 24 and 26 may include a single wire bent at its distal end to form an eyelet. Alternatively, at least one of the arms 24 and 26 may include a wire with a ring secured to its distal end. Alternatively, each of the arms 24 and 26 may include a sheath (not shown), having a wire (not shown) extending therethrough. One length of the wire may extend through the sheath and out of a distal end of the sheath. Outside of the sheath the wire may be bent and inserted back into the distal end of the sheath, leaving part of the bent portion of the wire exposed. The exposed part of the wire may form an eyelet. The sheath may be made of any suitable material, including a polymer such as polyimide, or polyethylene terephthalate.

The arms 24 and 26 may be more rigid than the arms 20 and 28. For example, the arms 24 and 26 may be made of the same material as the arms 20 and 28, but the arms 24 and 26 may be made thicker than the arms 20 and 28. Additionally or alternatively, the arms 24 and 26 may be made of a material having a higher stiffness coefficient than the material of the arms 20 and 28. For example, the arms 24 and 26 may be made of stainless steel, while the arms 20 and 28 may be made of Nitinol. Additionally or alternatively, the arms 24 and 26 may be stiffened by enclosing each of them within a stiffening sheath (not shown). The arms 24 and 26 may possess an internal bias causing the arms 24 and 26 to move radially outwardly away from a longitudinal axis of the end effector 16 in the absence of a constraining force.

Figure 1:
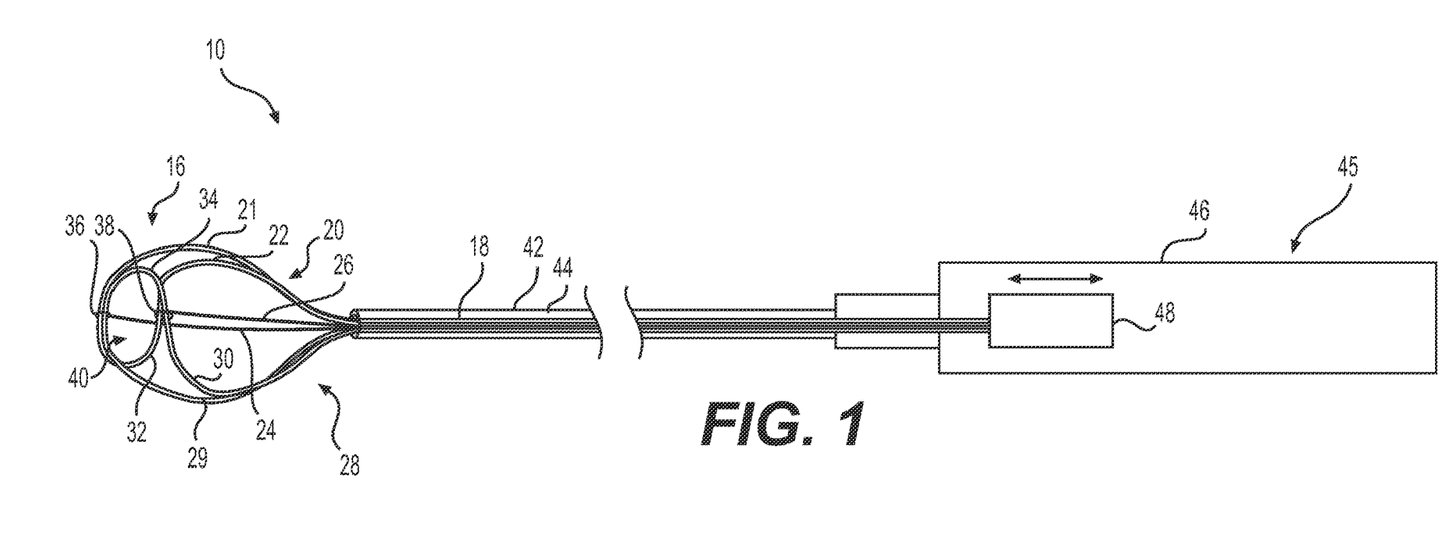
FIG. 1 is a schematic side view of a retrieval device including an end effector in an extended position and an expanded state, in accordance with aspects of the present disclosure.
Figure 4:
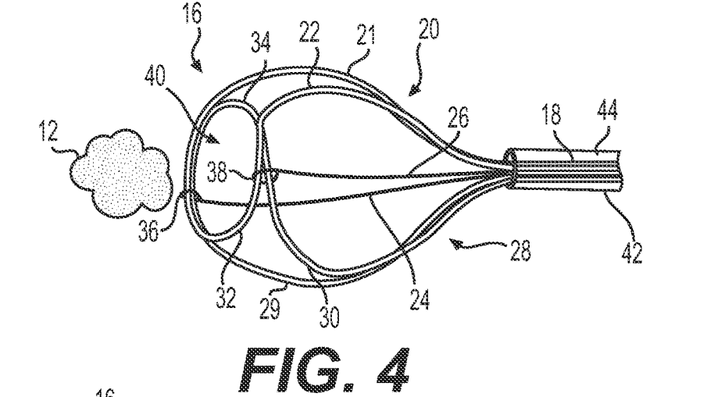
FIG. 4 is a side view of the end effector of the retrieval device of FIG. 1 in the extended position and the expanded state, and near an object to be retrieved, in accordance with aspects of the present disclosure.

The arms 20 and 28 may extend through the eyelets 36 and 38 of the arms 24 and 26. For example, the struts 22 and 30 may extend through the eyelet 38, and the struts 21 and 29 may extend through the eyelet 36. The curved end 32 may extend between the eyelets 36 and 38 on one side of the eyelets 36 and 38. The curved end 34 may extend between the eyelets 36 and 38 on the opposite side of the eyelets 36 and 38. As seen in FIGS. 1 and 4, the struts 21, 22, 29, and 30 may curve toward the eyelets 36 and 38. The curved struts 21, 22, 29, and 30 may form opposing sides of the end effector 16. The curved ends 32 and 34 may oppose each other and at least partially overlap, such that the curved ends 32 and 34 may form a front loop 40 of the end effector 16. The front loop 40 may define a central opening therein. The arms 20 and 28 may be slidable through the eyelets 36 and 38 to change the curvature of the struts 21, 22, 29, and 30, to change distances between the struts 21, 22, 29, and 30, and/or to change a diameter of the central opening of the front loop 40.

The end effector 16 may be movable between an extended position, where the end effector 16 is extended distally out of a distal end of the outer sheath 42, and a retracted position, where the end effector 16 is withdrawn proximally into a lumen 44 of the outer sheath 42 through the distal end of the outer sheath 42. The lumen 44 may extend longitudinally through the outer sheath 42. The outer sheath 42 may include, for example, a hollow tube. The outer sheath 42 may be made of a polymer material.

Figure 2:
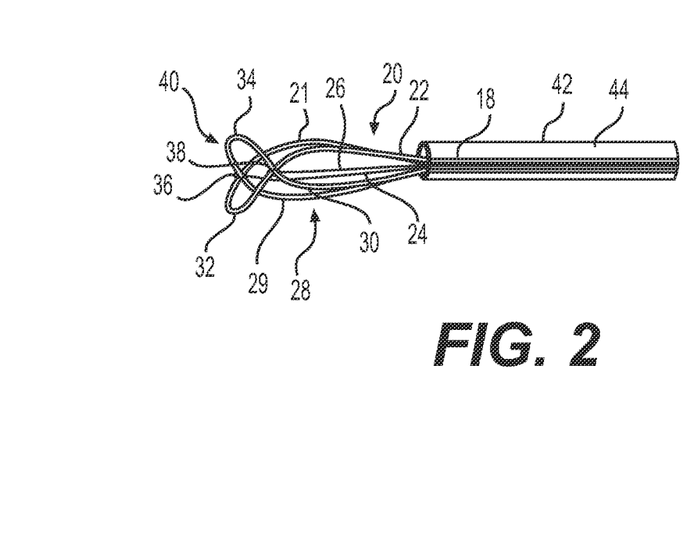
FIG. 2 is a side view of the end effector of the retrieval device of FIG. 1 in an intermediate state with the end effector in a partially extended/retracted position and a partially expanded/contracted state, in accordance with aspects of the present disclosure.
Figure 3:
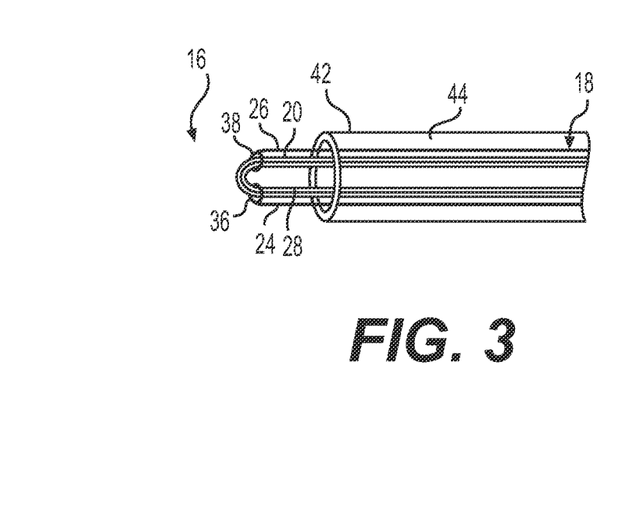
FIG. 3 is a side view of the end effector of the retrieval device of FIG. 1 in a retracted position and a contracted state, in accordance with aspects of the present disclosure.

In the extended position of the end effector 16, the arms 20, 24, 26, and 28 may expand radially outwardly into an expanded state, as shown in FIGS. 1 and 4. In the retracted position of the end effector 16, the arms 20, 24, 26, and 28 may contract radially inwardly into a collapsed or contracted state, as shown in FIG. 3. The end effector 16 may also be moved to partially extended/retracted positions, and/or partially expanded/retracted states, as shown in FIGS. 2 and 5-7. The end effector 16 may have an open end configuration in the expanded state and a closed end configuration in the collapsed or contracted state.

The drive member 18 may be used to move the end effector 16 relative to the outer sheath 42. According to one aspect, proximal ends of the arms 20, 24, 26, and 28 may be fixedly coupled to a distal end of the drive member 18. For example, the drive member 18 may include a cable or flexible cylindrical member.

Alternatively, proximal portions of the arms 20, 24, 26, and 28 may form at least part of the drive member 18. According to one aspect, two or more proximal portions of the arms 20, 24, 26, and 28 may be fixedly coupled, thus linking movement of those proximal portions. For example, proximal portions of the arms 20 and 28 may be fixedly coupled. Additionally or alternatively, proximal portions of the arms 24 and 26 may be fixedly coupled. It is also contemplated that proximal portions of the arms 20, 24, 26, and 28 may all be fixedly coupled.

According to another aspect, two or more proximal portions of the arms 20, 24, 26, and 28 may be uncoupled, allowing relative movement between those proximal portions. For example, proximal portions of the arm 20 and/or the arm 28 may be uncoupled from proximal portions of the arms 24 and 26. Additionally or alternatively, proximal portions of the arms 20, 24, 26, and 28 may all be uncoupled. Any combination of fixedly coupling and/or uncoupling of the proximal portions may be employed. For example, proximal portions of the arms 20 and 28 may be fixedly coupled, and proximal portions of the arms 24 and 26 may be fixedly coupled, while proximal portions of the arms 20 and 28 may be uncoupled from proximal portions of the arms 24 and 26. Additionally or alternatively, proximal portions of the arms 20 and 28 may be uncoupled from each other and from proximal portions of the arms 24 and 26, while proximal portions of the arms 24 and 26 may be fixedly coupled.

The retrieval device 10 may also include a handle assembly 45. The handle assembly 45 may include a sheath control portion 46 and an end effector control portion 48. The outer sheath 42 may be fixedly coupled to the sheath control portion 46. The drive member 18 may be fixedly coupled to the end effector control portion 48. One of the sheath control portion 46 and the end effector control portion 48 may be movable relative to the other. For example, the sheath control portion 46 may be moved distally relative to the end effector control portion 48, or the end effector control portion 48 may be moved proximally relative to the sheath control portion 46, to retract and contract the end effector 16. The sheath control portion 46 may be moved proximally relative to the end effector control portion 48, or the end effector control portion 48 may be moved distally relative to the sheath control portion 46, to extend and expand the end effector 16. The end effector control portion 48 may include one or more knobs, buttons, tabs, and/or any other suitable control structures (not shown) controlled by a user's hand or finger.

According to one aspect, when the drive member 18 includes one or more portions that are movable relative to one or more other portions of the drive member 18, the end effector control portion 48 may be configured to move the relatively movable portions individually or as a group, to control movement of the end effector 16. The end effector control portion 48 may include knobs, buttons, tabs, and/or any other suitable control structures (not shown), one such structure being fixedly coupled to, and configured to control, each of the proximal portions of the arms 20, 24, 26, and 28 that is movable relative to any of the other proximal portions. It is contemplated that the control structures may be moved individually or in unison to manipulate the end effector 16. For example, a part of the end effector control portion 48 may be coupled to proximal portions of the arms 20 and 28, and another part of the end effector control portion 48 may be coupled to proximal portions of the arms 24 and 26, such that the parts of the end effector control portion 48 may be relatively movable to move the arms 20 and 28 relative to the arms 24 and 26. Additionally or alternatively, the end effector control portion 48 may include two parts, one coupled to the proximal portion of the arm 20 and the other coupled to the proximal portion of the arm 28, such that the arms 20 and 28 may be relatively movable. The end effector control portion 48 may include any suitable number of parts for moving the arms 20, 24, 26, and 28.

A user may insert the distal portion of the retrieval device 10 into a patient and toward a target area within the patient containing an object the user wants to retrieve. For example, distal portions of the outer sheath 42 and the drive member 18, and the end effector 16, may be inserted directly into the patient and maneuvered to the target area. Alternatively, an introducer (not shown), such as a sheath or endoscope, may be inserted into the patient. The distal end of the introducer may be maneuvered to the target area. The retrieval device 10 may be inserted into a lumen of the introducer, maneuvered through the lumen, and at least partially extended from a distal end of the introducer into the target area. Alternatively, the retrieval device 10 may be pre-loaded into the introducer outside of the patient's body, such that the introducer and the retrieval device 10 may be inserted into the patient and maneuvered to the target area together. Maneuvering of the introducer and/or retrieval device 10 to the target area may be assisted by the use of any suitable visualization device, such as an imaging device at the distal end of the introducer.

During insertion of the retrieval device 10 into the patient, and/or maneuvering of the retrieval device 10 to the target area, the end effector assembly 16 may be in the retracted position and contracted state shown in FIG. 3. The reduced profile of the retracted and contracted end effector assembly 16 may make it easier to insert and maneuver the end effector assembly 16 through tortuous anatomy and/or small anatomical openings to the target area. The end effector assembly 16 may be retracted and contracted by moving the end effector control portion 48 proximally relative to the sheath control portion 46. For example, beginning with the end effector 16 extended and expanded, as shown in FIGS. 1 and 4, moving the end effector control portion 48 proximally relative to the sheath control portion 46 may move the drive member 18 proximally relative to the outer sheath 42, thus drawing a proximal portion of the end effector 16 into a distal end of the outer sheath 42. As the end effector 16 is drawn into the outer sheath 42, the end effector 16 may deform, as shown in FIG. 2. One or more of the arms 20, 24, 26, and 28 may become straighter. The arms 20, 24, 26, and 28 may move towards each other. The front loop 40 formed by the curved ends 32 and 34 may bend and/or fold. This may continue until the end effector 16 is housed within the outer sheath 42 in the manner shown in FIG. 3.

The distal end of the outer sheath 42 may be positioned near the object to be retrieved. The end effector 16 may be extended and expanded by moving the end effector control portion 48 distally relative to the sheath control portion 46. The end effector 16 may, for example, move from the state shown in FIG. 3 to the state shown in FIG. 2. As the end effector 16 is extended out of the outer sheath 42 the end effector 16 may expand radially outwardly due to its shape memory characteristics and/or inherent biasing. One or more of the arms 20, 24, 26, and 28 may become more curved. The arms 20, 24, 26, and 28 may move away from each other. The loop formed by the curved ends 32 and 34 may expand and/or flatten out. This may continue until the end effector 16 and the outer sheath 42 are expanded in the manner shown in FIG. 1.

Figure 6:
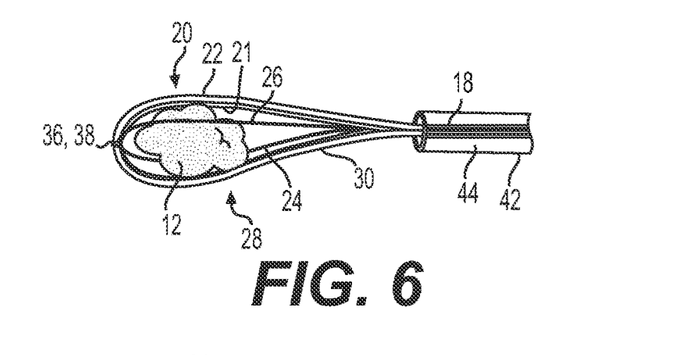
FIG. 6 is a side view of the end effector of the retrieval device of FIG. 1 in another partially contracted/expanded state around an object, in accordance with aspects of the present disclosure.
Figure 7:
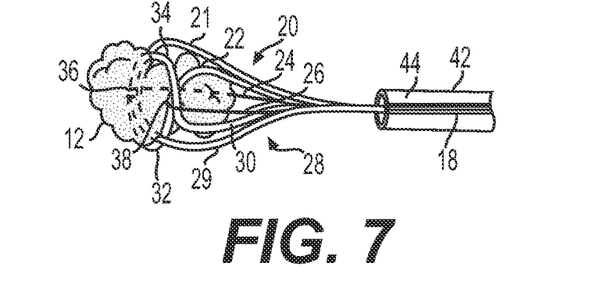
FIG. 7 is a side view of the end effector of the retrieval device of FIG. 1 in another partially contracted/expanded state around an object, in accordance with aspects of the present disclosure.

The user may maneuver the end effector 16 to position the object 12 within the end effector 16. With the end effector 16 extended and expanded, the front loop 40 may be at its widest diameter, and gaps between the arms 20, 24, 26 and 28 may be at their widest widths, facilitating entry of the object 12 into the end effector 16 through the front loop 40 or one of the gaps. In some instances, the entire object 12 may enter the end effector 16 (FIG. 6). In other instances, only part of the object 12 may enter the end effector 16 (FIG. 7).

Figure 5:
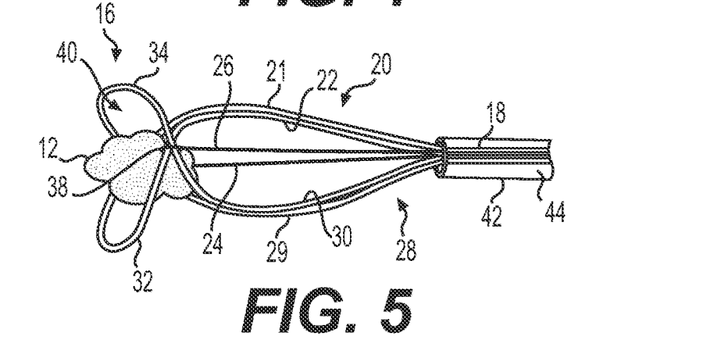
FIG. 5 is a side view of the end effector of the retrieval device of FIG. 1 in a partially contracted/expanded state around the object, in accordance with aspects of the present disclosure.
Figure 11:
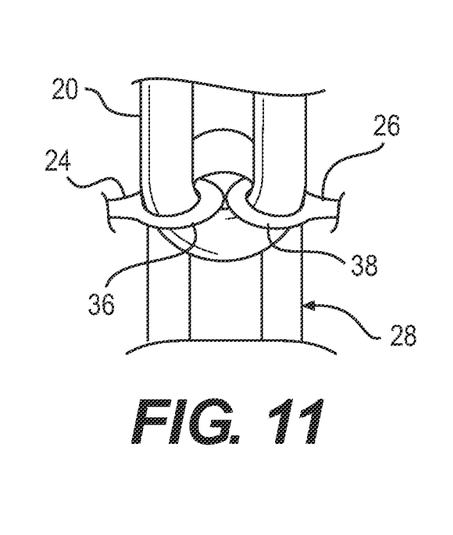
FIG. 11 is a close-up view of a closed distal end of the end effector of the retrieval device of FIG. 1, with the end effector in a contracted state, in accordance with aspects of the present disclosure.

The user may capture the object 12 in the end effector 16 by exerting a holding force on the object 12 using one or more parts of the end effector 16. According to one aspect, the user may move the end effector control portion 48 proximally relative to the sheath control portion 46 to move the drive member 18 proximally relative to the outer sheath 42, thus drawing the end effector 16 into the outer sheath 42. As the end effector 16 is drawn into the outer sheath 42, the end effector 16 may deform, as shown in FIG. 5. One or more of the arms 20, 24, 26, and 28 may become straighter. The arms 20, 24, 26, and 28 may move towards each other. The front loop 40 formed by the curved ends 32 and 34 may bend and/or fold. These movements may decrease the diameter of the front loop 40 and the widths of the gaps between the arms 20, 24, 26, and 28, limiting ways in which the object 12 may escape from within the end effector 16. As withdrawal of the end effector 16 into the outer sheath 42 continues, the arms 20, 24, 26, and 28 may forcibly engage the outer surface of the object 12. The diameter of the front loop 40 may decrease until the front loop 40 closes, with eyelets 36 and 38 drawn together into close proximity or into contact, giving the end effector 16 a closed distal end as shown in FIG. 6. FIG. 11 shows a close-up view (looking proximally from within end effector 16) of the closed distal end of FIG. 6. Tensile forces on the arms 20 and 28 may draw the reverse-bends of the arms 20 and 28 in opposite directions, bringing the reverse-bends toward each other. This movement of the arms 20 and 28 may draw the eyelets 36 and 38, and the rest of the arms 24 and 26, together. The closed distal end forms when further opposing movement of the reverse-bends of the arms 20 and 28 becomes obstructed by the portions of the eyelets 36 and 38 between the reverse-bends of the arms 20 and 28. The reverse-bends of the arms 20 and 28 may exert clamping forces on the eyelets 36 and 38, causing the reverse-bends of the arms 20 and 28 to interlock with the eyelets 36 and 38. Additional tensile forces on the arm 20 may bring the struts 21 and 22 closer together, thus increasing the curvature of the reverse-bend of the arm 20. Similarly, additional tensile forces on the arm 28 may bring the struts 29 and 30 closer together, thus increasing the curvature of the reverse-bend of the arm 28. As such, the reverse-bends of the arms 20 and 28 and the eyelets 36 and 38 may forcibly engage to an even greater degree.

In some instances, the object 12 may only be partially within the end effector 16, inhibiting full closing of the distal end of the end effector 16, as will be described in more detail below with reference to FIG. 7. It is also contemplated that during retraction of end effector 16, the distal end of the outer sheath 42 may exert a force on the object 12 and/or arms 20, 24, 26, and 28, further increasing the force of engagement between the object 12 and the arms 20, 24, 26, and 28. The user may then withdraw the retrieval device 10 from within the patient to remove the object 12 from the patient's body.

If part of the object 12 remains outside of the end effector 16 during its capture, at least some of the arms 20, 24, 26, and 28 may still be used to capture the object 12. For example, the front loop 40 may be positioned around an intermediate region of the object 12. As the end effector 16 is drawn into the outer sheath 42, the front loop 40 may fold (FIG. 5) due to pivoting movement of the curved ends 32 and 34 about the eyelets 36 and 38. The curved ends 32 and 34 may pivot to a point where the curved ends 32 and 34 and/or eyelets 36 and 38 may forcibly engage the intermediate portion of the object 12. Continued movement of the end effector 16 into the outer sheath 42 may close the front loop 40 tighter around the intermediate portion of the object 12, as shown in FIG. 7. The user may then withdraw the retrieval device 10 from within the patient to remove the object 12 from the patient's body.

The ability to move one or more of the arms 20, 24, 26, and 28 individually may assist with capturing the object 12. For example, the user may retract the arms 20 and 28 into the outer sheath 42 without retracting the arms 24 and 26 into the outer sheath. This may be possible when the drive member 18 includes proximal portions of the arms 20, 24, 26, and 28, and the end effector control portion 48 is configured to move the proximal portions of the arms 20 and 28 relative to the proximal portions of the arms 24 and 26. As the arms 20 and 28 are retracted, the front loop 40 may fold along a line extending between the eyelets 36 and 38 (FIG. 5) due to pivoting movement of the curved ends 32 and 34 about the eyelets 36 and 38. The curved ends 32 and 34 may pivot to a point where the curved ends 32 and 34 may clamp onto an object like first and second jaws of a forceps. The user may have the ability to reposition the object to make it easier to fully capture the object with the end effector 16.

Additionally or alternatively, as the arms 20 and 28 are retracted further into the outer sheath 42, the curved ends 32 and 34 may and/or eyelets 36 and 38 may engage the object 12 with increased force. If part of the object 12 is situated within the front loop 40, the curved ends 32 and 34 may forcibly engage the object 12 as shown in FIG. 7. The stiffness of the arms 24 and 26 may assist with holding the curved ends 32 and 34 such that the front loop 40 may be substantially planar and/or may extend substantially perpendicular to a central longitudinal axis of the end effector 16, as the curved ends 32 and 34 engage the object. If the object 12 is within the end effector 16, retraction of the arms 20 and 28 may bring the arms 20, 24, 26, and 28 radially inwardly to engage the object 12, and may close the front loop 40 such that the end effector 16 may be provided with the interlocked closed distal end as shown in FIGS. 6 and 11. This may allow the end effector 16 to capture the object 12 with at least a portion of the end effector 16 in the extended position.

It is also contemplated that one or more the arms 20, 24, 26, and 28 may be moved individually during one stage of capturing the object 12, and moved in unison with one or more others during another stage of capture of the object 12. For example, the arms 20 and 28 may be retracted while the arms 24 and 26 remain extended during a first stage of capturing the object 12. This may allow for capturing of the object 12 with the end effector 16 in an extended position. In some instances, retracting an end effector to initiate closing of the end effector around an object may cause the object to fall out of the end effector. Initiating closing of the end effector 16 around the object 12 prior to retracting the end effector 16 may reduce the likelihood of the object 12 falling out of the end effector 16 as closing of the end effector 16 begins. During a second stage, the arms 20, 24, 26, and 28 may be retracted in unison, allowing the distal end of the outer sheath 42 to engage the arms 20, 24, 26, and 28 to increase the holding force on the object 12.

While retraction and contraction of the end effector 16 into the outer sheath 42 may assist with capturing the object 12, extension and expansion of the end effector 16 after capturing the object 12 may facilitate release of the object 12 from the end effector 16. Releasing the object 12 may be performed by moving the parts of the end effector 16 in the opposite direction of that which has been described above for capturing the object 12. With the end effector 16 in the extended position and expanded state, the open front loop 40 may facilitate release of the object 12, as would the gaps between the arms 20, 22, 24, and 28.

Figure 8:
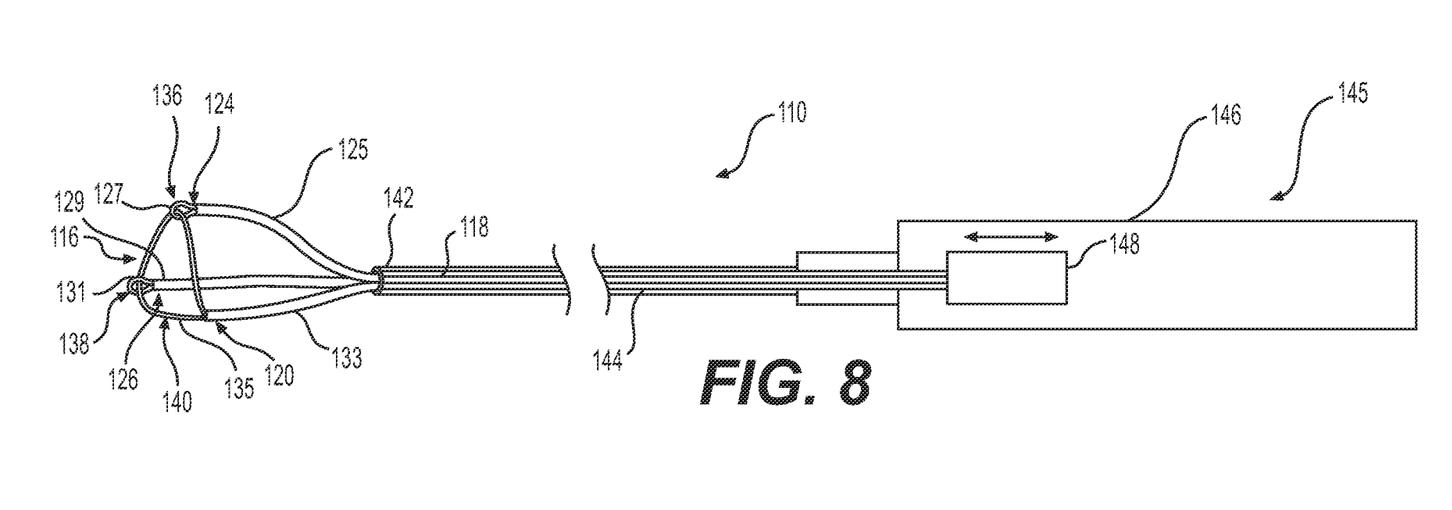
FIG. 8 is a schematic side view of another retrieval device including an end effector in an extended position and an expanded state, in accordance with aspects of the present disclosure.
Figure 9:
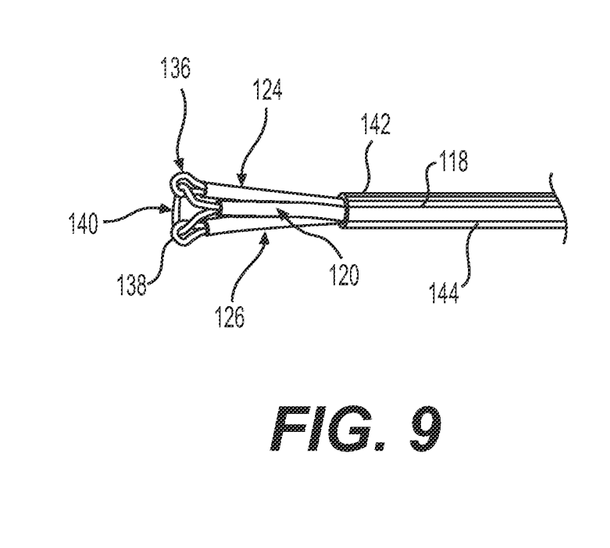
FIG. 9 is a side view of the end effector of the retrieval device of FIG. 8 in an extended position and a contracted state, in accordance with aspects of the present disclosure.
Figure 10:
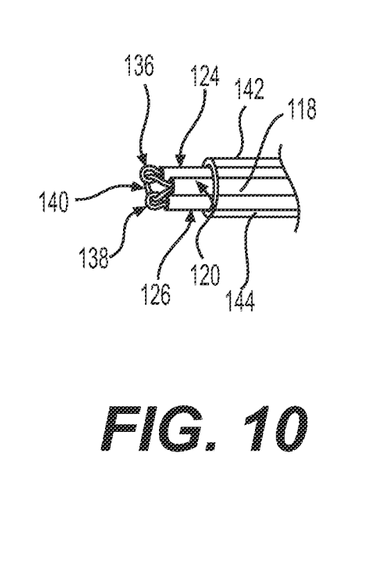
FIG. 10 is a side view of the end effector of the retrieval device of FIG. 9 in a retracted position and a contracted state, in accordance with aspects of the present disclosure.

FIGS. 8-10 show aspects of a retrieval device 110 having an end effector 116 configured to engage an object (not shown), such as the object 12 depicted in FIGS. 4-7. The retrieval device 110 may also include a drive member 118 configured to move the end effector 116. The end effector 116 may, for example, be selectively extended from and retracted into a distal portion of an outer sheath 142 by the drive member 118.

The end effector 116 may include arms 120, 124, and 126. The arms 120, 124, and 126 may form sides of the end effector 116. The arm 124 may include a sheath 125, and a wire 127 extending through the sheath 125. One length of the wire 127 may extend through the sheath 125 and out of a distal end of the sheath 125. Outside of the sheath 125 the wire 127 may be bent and inserted back into the distal end of the sheath 125, leaving part of the bent portion of the wire 127 exposed. The exposed part of the wire 127 may form an opening, loop, or eyelet 136 at the distal end of the arm 124. The sheath 125 may be made of any suitable material, including a polymer such as polyimide, or polyethylene terephthalate. The wire 127 may be made of stainless steel or Nitinol. The wire 127 may possess an internal bias causing the arm 124 to move radially outwardly away from a longitudinal axis of the end effector 116 in the absence of a constraining force. Additionally or alternatively, the sheath 125 may possess an internal bias causing the arm 124 to move radially outwardly. For example, a wall of the sheath 125 may include one or more struts or coils (not shown), to supply the internal bias. The arm 126 may include a sheath 129 and a wire 131 similar to the arm 124. Alternatively, one or more of the arms 124 and 126 may be similar to the arm 24 or the arm 26, in that it may be provided without a sheath.

The arm 120 may include a sheath 133 similar to the sheaths 125 and 129. The arm 120 may also include a wire 135 similar to the wires 127 and 131. The wire 135 and the sheath 133 may differ from the others in that the wire 135 may be selectively extended from and retracted into a distal portion of the sheath 133 by the drive member 118. In FIG.

8, the wire 135 is shown in an extended and/or expanded state. The wire 135 may extend through the eyelets 136 and 138, forming the front loop 140. The wire may be slidable through the eyelets 136 and 138 to pull the arms 124 and 126 radially inward when the wire 135 is retracted into the distal portion of the sheath 133 (FIGS. 9 and 10), and to permit the arms 124 and 126 to move radially outward when the wire 135 is extended out of the distal portion of the sheath 133. In an alternative example, the arm 120 may include the wire 135 without the sheath 133. In such an example, portions of the wire 135 at the proximal end of the end effector 116 may be capable of spreading apart to a greater degree than when the sheath 133 is present.

The end effector 116 may be movable between an extended position, where the end effector 116 is extended distally out of a distal end of the outer sheath 142, and a retracted position, where the end effector 116 is withdrawn proximally into a lumen 144 of the outer sheath 142 through the distal end of the outer sheath 142. The outer sheath 142 may be similar to the outer sheath 42 (FIGS. 1-7). In the extended position of the end effector 116, the arms 120, 124, and 126 may expand radially outwardly into an expanded state, as shown in FIG. 8. In the extended and expanded state, the end effector 116 may have an open end configuration, and may facilitate movement of an object into or out of the interior of the end effector 116 via openings formed between portions of the arms 120, 124, and 126. The arms 120, 124, and 126 may be drawn together into a contracted state while the end effector 116 is in an extended state, as shown in FIG. 9. In this extended and contracted state, the end effector 116 may have a closed end configuration, and may forcibly engage an object to keep the object in the interior of the end effector 116. The arms 120, 124, and 126 may also be contracted and retracted as shown in FIG. 10. Such a movement may enhance the force of engagement between the arms 120, 124, and 126 and the object due to the contracting force exerted on the arms 120, 124, and 126 by the outer sheath 142. It should be appreciated that the end effector 116 may also be moved to partially extended/retracted positions, and/or partially expanded/retracted states.

It is contemplated that the closed end configuration of the end effector 116 may be reached when the loop 140 has been pulled so tight that the eyelets 136 and 138 are drawn adjacent to or into contact with each other, and further closure of the loop 140 is prevented by the portions of the eyelets 136 and 138 within the loop 140. This leads to an interlocking of the eyelets 136, 138 and 140 that forms the closed end configuration.

In an alternative example, one of arms 124 and 126 may be omitted, leaving the end effector 116 with two arms (the second arm being the arm 120). Operation of the end effector 116 in this example may be similar to operation in the example where both of the arms 124 and 126 are present, in that the exertion of a tensile force on the wire 135 of the arm 120 may close the loop 140, and bring the one of the arms 124 and 126 toward the arm 120.

The drive member 118 may be used to move the end effector 116 relative to the outer sheath 142. For example, proximal ends of the arms 120, 124, and 126 may be fixedly coupled to a distal end of the drive member 118. The drive member 118 may include, for example, a cable or flexible cylindrical member. In one exemplary configuration, proximal ends of sheaths 125, 129, and 133, and wires 127 and 131 may be fixedly coupled to the distal end of a first portion of the drive member 118. Alternatively, wires 127 and 131 may be fixedly coupled to the distal ends of sheaths 125 and 129. The proximal end of the wire 135 may be coupled to the distal end of a second portion of the drive member 118, the second portion being uncoupled from the first portion, so as to allow wire 135 to move relative to sheaths 125, 129, and 133, and wires 127 and 131.

The retrieval device 110 may also include a handle assembly 145. The handle assembly 145 may include a sheath control portion 146 and an end effector control portion 148. The outer sheath 142 may be fixedly coupled to the sheath control portion 146. The drive member 118 may be fixedly coupled to the end effector control portion 148. One of the sheath control portion 146 and the end effector control portion 148 may be movable relative to the other. For example, the sheath control portion 146 may be moved distally relative to the end effector control portion 148, or the end effector control portion 148 may be moved proximally relative to the sheath control portion 146, to retract and contract the end effector 116. The sheath control portion 146 may be moved proximally relative to the end effector control portion 148, or the end effector control portion 148 may be moved distally relative to the sheath control portion 146, to extend and expand the end effector 116. The end effector control portion 148 may include one or more knobs, buttons, tabs, and/or any other suitable control structures (not shown) controlled by a user's hand or finger.

According to one aspect, when the drive member 118 includes one or more portions that are movable relative to one or more other portions of the drive member 118, the end effector control portion 148 may be configured to move the relatively movable portions individually or as a group, to control movement of the end effector 116. For example, a part of the end effector control portion 148 may be coupled to proximal portions of sheaths 125, 129, and 133, and wires 127 and 131, and another part of the end effector control portion 148 may be coupled to the proximal portion of the wire 135, such that the parts of the end effector control portion 148 may be relatively movable to move the wire 135 relative to sheaths 125, 129, and 133, and wires 127 and 131, to contract the end effector 116 and/or to allow it to expand.

Alternatively, a part of the end effector control portion 148 may be coupled to proximal portions of sheaths 125 and 129, and wires 127 and 131, and another part of the end effector control portion 148 may be coupled to the proximal portions of the sheath 133 and the wire 135, such that the parts of the end effector control portion 148 may be relatively movable to move the sheath 133 and wire 135 relative to sheaths 124 and 129, and wires 127 and 131, to contract the end effector 116 and/or to allow it to expand. In such a configuration, it should be appreciated that yet another part of the end effector control portion 148 may be configured to move the wire 135 relative to the sheath 133 to expand and contract the loop 140. In any of the configurations described above, the steps associated with using the end effector 116 to retrieve and release an object are similar to the steps described with respect to end effector 16.

It will be apparent to those skilled in the art that various modifications and variations can be made in the disclosed systems and processes without departing from the scope of the disclosure. Other aspects of the disclosure will be apparent to those skilled in the art from consideration of the specification and practice of the features disclosed herein. It is intended that the specification and examples be considered as exemplary only.

We claim:
1. A retrieval device, comprising:
a sheath having a distal end; and an end effector movable relative to the distal end of the sheath, the end effector including:
- a first arm including a first opening at a distal portion of the first arm;
- a second arm including a second opening at a distal portion of the second arm;
- a third arm slidably received in the first and the second openings; and
- a fourth arm slidably received in the first and second openings;

wherein a distal portion of the third arm and a distal portion of the fourth arm form a loop, a size of the loop being adjustable by movement of the end effector relative to the sheath;

wherein the third arm and the fourth arm are movable relative to the sheath without moving the first arm and the second arm.

2. The retrieval device of claim 1, wherein the third arm includes a pair of proximal portions connected by a curved and unconstrained distal end, and wherein one proximal portion of the pair of proximal portions passes through the first opening and the other proximal portion of the pair of proximal portions passes through the second opening.

3. The retrieval device of claim 1, wherein the first arm and the second arm are more rigid than the third arm and the fourth arm.

4. The retrieval device of claim 1, wherein the third arm and the fourth arm are biased radially outward and form an expanded configuration of the end effector when unconstrained by the sheath.

5. The retrieval device of claim 1, wherein the third arm and the fourth arm form opposing sides of the end effector, the distal portion of the third arm forming one side of the loop and the distal portion of the fourth arm forming another opposite side of the loop.

6. The retrieval device of claim 1, wherein the size of the loop changes by bending or folding of the end effector when the end effector moves relative to the sheath.

7. The retrieval device of claim 1, wherein the third arm is configured to slide through the first opening and the second opening in a first direction and the fourth arm is configured to slide through the first opening and the second opening in a second direction opposite the first direction.

8. The retrieval device of claim 1, wherein the end effector is configured to transition between an expanded configuration and a collapsed configuration by moving the end effector relative to the sheath, and wherein in the collapsed configuration, the first and second openings are closer together than in the expanded configuration.

9. The retrieval device of claim 1, wherein the loop defines a central opening unobstructed by the first arm and the second arm, and wherein the central opening is configured to receive at least a portion of an object to be retrieved by the end effector.

10. The retrieval device of claim 1, wherein the retrieval device further comprises a handle assembly configured to move the end effector relative to the distal end of the sheath.

11. The retrieval device of claim 10, wherein the end effector is coupled to the handle assembly by a drive member.

12. A retrieval device, comprising:
a sheath having a distal end; and
an end effector movable relative to the distal end of the sheath, the end effector including a first arm, a second arm, a third arm, and a fourth arm, wherein first and second openings on the first and second arms, respectively, of the end effector each receive the third arm and the fourth arm of the end effector:

wherein each of the third arm and the fourth arm includes a pair of proximal portions connected by a curved and unconstrained distal end, the curved and unconstrained distal ends of the third and fourth arms collectively forming a loop;

wherein the end effector is configured to transition between an expanded configuration and a collapsed configuration by moving the end effector relative to the sheath, a size of the loop being reduced by retracting the first and second arms proximally within the sheath; and wherein the curved and unconstrained distal ends of the third and fourth arms are configured to pivot about the first and second openings when the end effector transitions to the collapsed configuration.

13. The retrieval device of claim 12, wherein one proximal portion of the pair of proximal portions of the third arm passes through the first opening and the other proximal portion of the pair of proximal portions of the third arm passes through the second opening, so that the curved and unconstrained distal end of the third arm extends between the first and second openings in a first direction.

14. The retrieval device of claim 13, wherein one proximal portion of the pair of proximal portions of the fourth arm passes through the first opening and the other proximal portion of the pair of proximal portions of the fourth arm passes through the second opening, so that the curved and unconstrained distal end of the fourth arm extends between the first and second openings in a second direction opposite the first direction.

15. The retrieval device of claim 12, wherein in the collapsed configuration, the first and second openings contact each other.

16. A retrieval device, comprising:
a sheath defining a distal end;
an end effector movable relative to the distal end of the sheath, the end effector including:
- a first arm including a first opening at a distal portion of the first arm;
- a second arm including a second opening at a distal portion of the second arm;
- a third arm received in the first and the second openings, the third arm being configured to slide through the first opening and the second opening in a first direction when the end effector moves proximally relative to the sheath; and
- a fourth arm received in the first and second openings, the fourth arm being configured to slide through the first opening and the second opening in a second direction opposite the first direction when the end effector moves proximally relative to the sheath;

wherein a distal portion of the third arm and a distal portion of the fourth collectively form a loop, a size of the loop being adjustable by transitioning between an expanded configuration and a collapsed configuration by moving the end effector relative to the sheath;

wherein the third arm and the fourth arm are movable relative to the sheath without moving the first arm and the second arm.

17. The retrieval device of claim 16, wherein the third and fourth arms each comprise a shape memory material, and the first and second arms are more rigid than the third and fourth arms.

18. The retrieval device of claim 16, wherein the third arm and the fourth arm form opposing sides of the end effector, the distal portion of the third arm forming one side of the loop and the distal portion of the fourth arm forming another opposite side of the loop.

* * * * *